(12) United States Patent
Xu

(10) Patent No.: US 9,180,395 B2
(45) Date of Patent: Nov. 10, 2015

(54) POROUS THIN FILMS

(75) Inventor: Ting Xu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 493 days.

(21) Appl. No.: 13/508,984

(22) PCT Filed: Nov. 20, 2010

(86) PCT No.: PCT/US2010/056467
§ 371 (c)(1),
(2), (4) Date: Jan. 25, 2013

(87) PCT Pub. No.: WO2011/060229
PCT Pub. Date: May 19, 2011

(65) Prior Publication Data
US 2013/0129972 A1    May 23, 2013

Related U.S. Application Data

(60) Provisional application No. 61/260,790, filed on Nov. 12, 2009.

(51) Int. Cl.
*C07K 7/64* (2006.01)
*B01D 39/16* (2006.01)
*A61K 47/48* (2006.01)
*C07K 5/062* (2006.01)
*C07K 7/06* (2006.01)

(52) U.S. Cl.
CPC ...... *B01D 39/1692* (2013.01); *A61K 47/48215* (2013.01); *C07K 5/06026* (2013.01); *C07K 7/06* (2013.01); *C07K 7/64* (2013.01); *C08L 2203/02* (2013.01); *Y10T 428/24322* (2015.01)

(58) Field of Classification Search
CPC .................................. C07K 7/06; C07K 7/64
See application file for complete search history.

(56) References Cited

U.S. PATENT DOCUMENTS

| | | |
|---|---|---|
| 2004/0024176 A1 | 2/2004 | Ghadiri |
| 2005/0124535 A1 | 6/2005 | McGimpsey |
| 2006/0211615 A1 | 9/2006 | Zhang et al. |
| 2008/0124535 A1 | 5/2008 | Grater |
| 2010/0291828 A1* | 11/2010 | Reches et al. ................. 442/340 |
| 2012/0021954 A1* | 1/2012 | Gazit et al. ..................... 506/18 |

OTHER PUBLICATIONS

Couet et al., 2005, Peptide-Polymer Hybrid Nanotubes, Angew. Chem. Int. Ed., 44: 3297-3301.*
Thurn-Albrecht et al., 2000, Ultrahigh-Density Nanowire Arrays Grown in Self-Assembled Diblock Copolymer Templates, Science, 290: 2126-2129.*
International Search Report and Written Opinion, dated Jan. 18, 2011, issued in related International Patent Application No. PCT/US2010/056467, filed Nov. 12, 2010.
Couet et al., "Conjugating self-assembling rigid rings for flexible polymer coils for the design of organic nanotubes," 2006, Soft Matter, 2, pp. 1005-1014.

* cited by examiner

*Primary Examiner* — Amber D Steele
(74) *Attorney, Agent, or Firm* — Lawrence Berkeley National Laboratory

(57) ABSTRACT

Compositions of porous thin films and methods of making are provided. The methods involve self-assembly of a cyclic peptide in the presence of a block copolymer.

15 Claims, 15 Drawing Sheets

(a)

(b)

(c)

(a)

(b)

(a)

(b)

(a)

(b)

Zoom-in view of the center of the test membrane (a)

(b)

(c)

POROUS THIN FILMS

CROSS-REFERENCE TO RELATED APPLICATIONS

This present application is the U.S. National Stage entry under §371 of International Application No. PCT/US2010/056467, filed Nov. 12, 2010, which claims the benefit of U.S. Provisional Application No. 61/260,790, filed Nov. 12, 2009, which are incorporated in their entirety herein for all purposes.

STATEMENT AS TO RIGHTS TO INVENTIONS MADE UNDER FEDERALLY SPONSORED RESEARCH OR DEVELOPMENT

This invention was made with government support under Contract No. DE-AC02-05CH11231 awarded by the U.S. Department of Energy. The government has certain rights in this invention.

BACKGROUND OF THE INVENTION

There are growing demands to fabricate polymeric thin films with vertically aligned sub-nanometer channels for applications including carbon capture, gas separation, water desalination, batteries, fuel cell membranes, and solar-fuel conversion. Obtaining molecular level control over the pore size, shape and surface chemistry is a critical bottleneck, and has been investigated across many disciplines. Inorganic or hybrid porous materials, like zeolites and metal organic frameworks, where pore size can be readily tailored from a few tenths to several nanometers, have achieved some success along these lines. However, it remains a challenge to orient the channels over macroscopic distances and to process these materials on flexible substrates.

Polymers, on the other hand, are readily processed at low cost as thin films or multilayered laminates with little, if any, constraints on chemical structure and thickness of the individual layers. Hypercrosslinked polymer networks can provide pores as small as a few tenths of nanometers, but the size distribution of the pores is broad and the spatial arrangement is random which impedes selective transport. Alternatively, by using block copolymers (BCPs), it is now routine to produce nanoporous thin films with nearly monodisperse aligned pores as small as 3 nm. However, even the smallest pore size obtained in a BCP thin film is too large for the selective molecular transport required in advanced applications including the aforementioned areas.

Composite films have been fabricated using preformed nanotubes, like carbon nanotubes (CNTs). However, there are no effective means to orient preformed nanotubes normal to the surface over macroscopic distances. Thus, vertically aligned CNT forests have been grown on substrates, yet it remains non-trivial to backfill with matrix materials between CNTs to achieve lift-off from the underlying substrate generating through channels. CNTs prepared via this route are still subject to some degree of heterogeneity in their pore size distribution, which may be a further limiting factor in their implementation as selective membranes. Interior modification of preformed nanotubes to enhance selectively also represents a significant hurdle.

In contrast to CNTs, sub-nanometer tubular materials with precise control over the pore size, shape and surface chemistry can be produced by assembling organic motifs, like cyclic peptides, dendrimers, DNA, surfactants and rosettes. Unlike preformed-nanotubes such as CNTs, the formation of nanotubes based on organic subunits is reversible, as they are governed by specific inteimolecular interactions, like hydrogen bonding or electrostatic interactions. A directed, synergistic co-assembly of nanotube subunits and BCPs may allow one to direct the formation of nanotubes within the nanoscopic domains established by the BCPs so as to manipulate the spatial organization and macroscopic orientation of nanotubes. This process takes full advantage of nanoscopic assembly of BCPs and the reversibility of organic nanotube growth and is compatible with existing technologies for thin film fabrication. It completely eliminates the need to prepare nanotubes of uniform length, since the number of subunits comprising the nanotube can easily be varied so that the nanotube length is tailored to be equal to the film thickness, thus producing porous films with nanotubes that span the entire film. This new strategy also circumvents all impediments associated with aligning and organizing high aspect ratio nano-objects normal to the surface. Surprisingly, the present invention meets this and other needs.

BRIEF SUMMARY OF THE INVENTION

In one embodiment, the present invention provides a method of making a porous thin film, including contacting a substrate with a mixture of a plurality of cyclic peptide conjugates each having a cyclic peptide and a conjugate polymer covalently linked to the cyclic peptide. The mixture also includes a block copolymer having a first block able to bind to the conjugate polymer and a second block that does not substantially bind to the conjugate polymer. The method also includes annealing the mixture such that the cyclic peptide conjugates self-assemble to form a cyclic peptide nanotube perpendicular to the substrate and extending from a top surface to a bottom surface of the porous thin film.

In another embodiment, the present invention also provides a porous thin film composition prepared by the method of the present invention.

In other embodiments, the present invention provides a porous thin film composition including a cyclic peptide nanotube having a plurality of cyclic peptide polymer conjugates each including a cyclic peptide and a conjugate polymer covalently linked to the cyclic peptide, wherein the cyclic peptide nanotube extends from a bottom surface of the porous thin film to a top surface of the porous thin film, and wherein the cyclic peptide nanotube has a pore diameter of about 0.5 to about 3 nm. The porous thin film composition also includes a block copolymer having a first block able to bind to the conjugate polymer and a second block that does not substantially bind to the conjugate polymer, wherein the porous thin film has a thickness of from about 10 nm to about 1000 nm.

BRIEF DESCRIPTION OF THE DRAWINGS

FIG. 2(*a*) shows the amide A region of the FTIR spectra of a blend of 8CP- PEO/CSM (2:10 wt ratio) during a heating (dash line, red) and cooling cycle (solid line, blue) from 30 to 180° C. FIG. 2(b) shows the fraction of 8CPNs based on the absorbance at 3277 cm$^{-1}$ as a function of temperature for 8CP alone (Δ) and a blend of 8CP-PEO/CSM (●) during the heating (red) and cooling (blue) cycle. Thermoreversible nanotube growth can be clearly observed.

FIG. 3(a) is the AFM height image of ~32 nm thin films of 8CP-PS/LSM (3:10 wt ratio), where PS-covered CPNs phase separate from LSM. This increased the interfaces between PS and PMMA as schematically shown. Individual PS-covered CPNs laying parallel to the surface can be clearly seen. FIG. 3(b) is a HAADF-STEM image of a ~32 nm thin film of PEO-8CP/LSM (3:10 wt ratio), where PEO-covered CPNs are selectively sequestered in the PMMA lamellae. The bright and dark lamellae correspond to PS and PMMA microdomains, respectively. FIG. 3(c) show the EELS spectra that identify the PS, PMMA and PEO regions, respectively.

FIG. 4(a) is the AFM phase image of a ~32 nm thin film of PEO-8CP/CSM (2:10 wt ratio). The dark core corresponds to PEO-covered 8CPNs. FIG. 4(b) is the TEM image of an in-plane view of a similar PEO-8CP/CSM (2:10 wt ratio) thin film. Circles indicate the CPNs aligned parallel to the electron beam. Inset shows the zoomed-in image of an in-plane view of one 8CPN. FIG. 4(c) is the GISAXS pattern of a ~32 nm thin film of PEO-8CP/CSM at an incident angle of $\alpha_c$=0.19°. FIG. 4(d) shows the $q_y$ scans at $q_z$=0.025A-1 for thin films of PEO-8CP/CSM and CSM. Upon incorporation of PEO-8CP, the lateral spacing increases ~3 nm from 38 nm to 41 nm. The combined GISAXS, AFM and TEM results confirmed incorporation of one PEO-8CPN per PMMA cylindrical microdomain at a PEO-8CP:CSM ratio of 2:10 by weight.

FIG. 5(a) is a photo of the transport measurement setup. FIG. 5(b) shows the UV-vis absorption spectra of HPTS buffer solution before and after the acidic buffer solution was deposited onto the PEO-8CPN/CSM and PEO/CSM thin films.

DETAILED DESCRIPTION OF THE INVENTION

I. General

Figure 1:
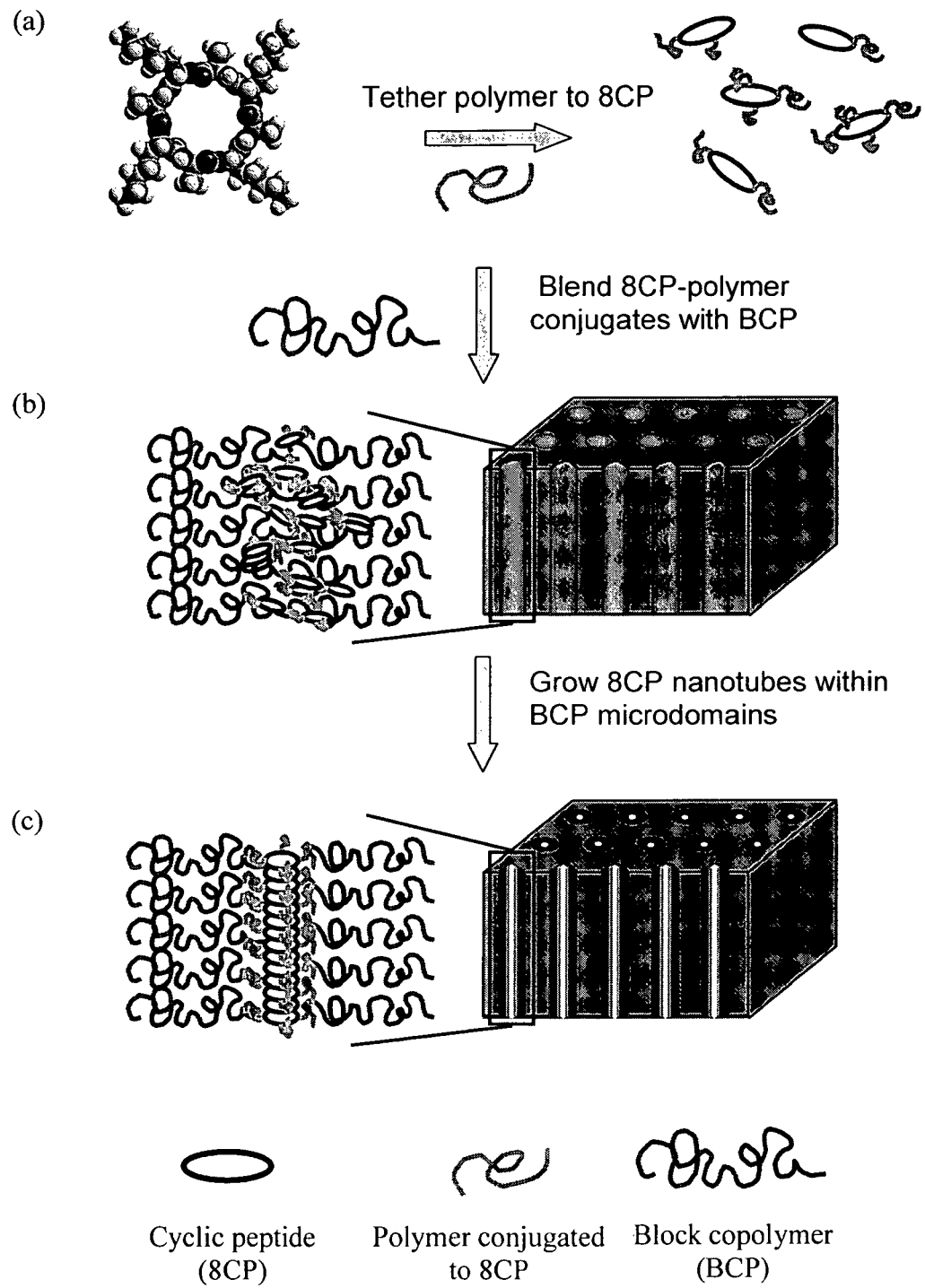
FIG. 1 shows the process to generate sub-nanometer porous films via directed co-assembly of cyclic peptide (CP) and a block copolymer (BCP) forming cylindrical microdomains. Polymers are first covalently linked to the side chains of 8CPs to form 8CP-polymer conjugates (FIG. 1(*a*)). The attached polymers effectively mediate the interactions between 8CPs and BCP. Upon blending with BCPs, 8CP-polymer conjugates are selectively sequestered within one BCP component (FIG. 1(*b*)) and subsequently, assemble into nanotubes spanning the entire film thickness to produce sub-nanometer porous films (FIG. 1(*c*)).

The present invention describes a porous thin film having hexagonally distributed pores throughout the film, where the pores are of uniform diameter and extend through the thickness of the porous thin film. The porous thin film is prepared by self-assembling conjugates of a cyclic peptide and a polymer in the presence of a block copolymer where one block has an affinity for the conjugate polymer and the second block has substantially no affinity for the conjugate polymer. The resulting cyclic peptide nanotube extends through the thickness of the porous thin film and is perpendicular to the film surface.

II. Definitions

"Porous thin film" refers to a film about 10 to about 1000 nm thick having a plurality of pores about 0.5 to about 5 nm in diameter where the pores are perpendicular to a surface of the film and extend through the full thickness of the film. The film includes cyclic peptide nanotubes that form the pores, and a block copolymer.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Cyclic peptide" refers to a peptide chain having from about 6 to about 20 amino acids linked to form a macrocycle. The cyclic peptide can be covalently linked to a polymer, a conjugate polymer, to form a cyclic peptide conjugate. The cyclic peptides and cyclic peptide conjugates can self-assemble to form a cyclic peptide nanotube, where the cyclic peptides are stacked one on top of another.

"Block copolymer" refers to a polymer prepared from at least two different monomer units, where the first monomer unit forms a first block, and a second monomer unit forms a second block of the block copolymer. The block copolymer can be prepared from monomers that include, but are not limited to, acrylates, methacrylates, acrylamides, methacrylamides, and styrenes.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Hydrophilic polymer" refers to a polymer having an affinity for aqueous solutions. Examples of hydrophilic polymers include, but are not limited to, polyethylene oxide (PEO).

"Coating polymer" refers to a polymer coating on the substrate that improves the adhesion of the porous thin film to the substrate. Examples of the coating polymer include, but are not limited to, a random copolymer of styrene, methylmethacrylate and benzocyclobutene.

"Random copolymer" refers to a polymer having at least two different monomer groups that are distributed randomly throughout the polymer backbone. The random copolymers can be prepared from monomers that include, but are not limited to, acrylates, methacrylates, acrylamides, methacrylamides, styrenes, and cyclobutenes.

III. Porous Thin Films

The present invention provides a method of making a porous thin film having uniform pores that extend through the thickness of the film and are perpendicular to the film surface.

In some embodiments, the present invention provides a method of making a porous thin film, including contacting a substrate with a mixture of a plurality of cyclic peptide conjugates each having a cyclic peptide and a conjugate polymer covalently linked to the cyclic peptide. The mixture also includes a block copolymer having a first block able to bind to the conjugate polymer and a second block that does not substantially bind to the conjugate polymer. The method also includes annealing the mixture such that the cyclic peptide conjugates self-assemble to form a cyclic peptide nanotube perpendicular to the substrate and extending from a top surface to a bottom surface of the porous thin film.

The substrate can be any suitable substrate. For example, the substrate can include, but are not limited to, metals, semiconductors (Si, Ga, Ge, etc.), inorganic materials, glass, and polymers. The substrate surface can also be modified to improve adhesion of the block copolymer and cyclic peptide conjugate to the substrate. Modification of the substrate surface can be via self-assembled monolayer or coating with another polymer layer. In some embodiments, the method also includes coating the surface of the substrate with a coating polymer prior to contacting with the mixture, the coating polymer including a random copolymer of styrene (S), methylmethacrylate (MMA) and benzocyclobutene (BCB). In other embodiments, the method also includes annealing the coating polymer.

Amino acids useful in the cyclic peptides of the present invention include naturally-occurring amino acids, as well as those amino acids that are later modified, e.g., γ-carboxyglutamate and O-phosphoserine, as well as unnatural amino acids. Naturally-occurring α-amino acids include (shown with the corresponding 3 letter and single letter codes), without limitation, alanine (Ala, A), cysteine (Cys, C), aspartic acid (Asp, D), glutamic acid (Glu, E), phenylalanine (Phe, F), glycine (Gly, G), histidine (His, H), isoleucine (Ile, I), arginine (Arg, R), lysine (Lys, K), leucine (Leu, L), methionine (Met, M), asparagine (Asn, N), proline (Pro, P), glutamine (Gln, Q), serine (Ser, S), threonine (Thr, T), valine (Val, V), tryptophan (Trp, W) and tyrosine (Tyr, Y). Stereoisomers of a naturally-occurring α-amino acids include, without limitation, D-alanine (DAla, a), D-cysteine (DCys, c), D-aspartic acid (DAsp, d), D-glutamic acid (DGlu, e), D-phenylalanine (DPhe, f), D-histidine (DHis, h), D-isoleucine (DIle, i), D-arginine (DArg, r), D-lysine (DLys, k), D-leucine (DLeu, l), D-methionine (DMet, m), D-asparagine (DAsn, n), D-proline (DPro, p), D-glutamine (DGln, q), D-serine (DSer, s), D-threonine (D-Thr, t), D-valine (D-Val, v), D-tryptophan (DTrp, w) and D-tyrosine (DTyr, y).

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups. Suitable unnatural amino acids include, without limitation, α-aminohexanedioic acid (Aad), acid (Abu), 3-aminobenzoic acid (3Abz), azetidine-2-carboxylic acid (Aca), 1-aminocyclobutane-1-carboxylic acid (Acb), α-amino-3-chloro-4,5-dihydro-5-isoazoleacetic acid (Acdi), 4-amino-4-carboxy-1,1-dioxo-tetrahydrothiopyran (Acdt), 1-amino-1-cyclohexane carboxylic acid (Ach), 1-aminocyclopentane-1-carboxylic acid (Acp), 1-aminocyclopropane-1-carboxylic acid (Acpc), 4-amino-4-carboxytetrahydropyran (Actp), 8-amino-1,4-dioxaspiro[4.5]decane-8-carboxylic acid (Aecc), (S)-2-amino-4-guanidino-butanoic acid (Agb), allylglycine (Agl), (S)-2-amino-3-guanidino-propanoic acid (Agp), 2-aminoheptanoic acid (Aha), 1-amino-1-(4-hydroxycyclohexyl) carboxylic acid (Ahch), α-aminoisobutyric acid (Aib), 2-aminoindane-2-carboxylic acid (Aic), 1-amino-1-(4-ketocyclohexyl) carboxylic acid (Akch), 2-aminooctanoic acid (Aoa), 2-amino-2-naphthylacetic acid (Ana), 1-amino-1-(3-piperidinyl) carboxylic acid (3Apc), 1-amino-1-(4-piperidinyl) carboxylic acid (4Apc), 2-amino-3-(4-piperidinyl) propionic acid (4App), homoarginine (HoArg), Nα-methyl-arginine ((NMe)Arg), Nα-methyl-aspartic acid ((NMe)Asp), α-aminooctanedioic acid (Asu), (R)-2-amino-3-(2-carboxyethylsulfanyl)propanoic acid (Bec), 4,4'-biphenylalanine (Bipa), (R)-2-amino-3-(carboxymethylsulfanyl)propanoic acid (Bmc), 4-carboxymethoxyphenylalanine (Bmp), 4-benzoylphenylalanine (Bpa), 3-benzothienylalanine (Bta), 5H-thiazolo[3,2-a]pyridine-3-carboxylic acid (Btd), β-t-butyl-alaine (Bua), α-tert-butylglycine (Bug), 4-cyano-2-aminobutyric acid (Cab), cyclobutylalanine (Cba), cyclohexylalanine (Cha), homocyclohexylalanine (HoCha), α-cyclohexylglycine (Chg), citrulline (Cit), homocitrulline (HoCit), cyclopropylalanine (Cpa), cyclopentylglycine (Cpeg), 3-carboxymethyl-1-phenyl-1,3,8-triazaspiro[4,5]decan-4-one (Cptd), homocysteine (HoCys), α,γ-diaminobutyric acid (Dbu), diethylglycine (Deg), 3,3-diphenyl-alanine (Dpa), di-n-propylglycine (Dpg), α,β-diaminopropionic acid (Dap), α,γ-diaminobutyric acid (Dab), 2-furyl-Alanine (Fua), homoarginine (HoArg), hydroxyproline (Hyp), O-benzyl-hydroxyproline (Hyp(Bzl)), homoleucine (HoLeu), 2-Indanylglycine (Ing), methionine sulfoxide (Met(O)), methionine methylsulfonium (Met (S-Me)), 3-(1-naphthyl)alanine (Nal1), 3-(2-naphthyl)alanine (Nal2), 3-(carboxymethylamino)propanoic acid (Nglu), nipecotic acid (Nip), isonipecotic acid (IsoNip), norleucine (Nle), norvaline (Nva), octahydroindole-2-carboxylic acid (Oic), ornithine (Orn), 2-pyridylalanine (2 Pal), 3-(3-pyridyl)alanine (3 Pal), 3-(4-pyridyl)alanine (4 Pal), penicillamine (Pen), homophenylalanine (HoPhe), Nα-methyl-phenylalanine ((NMe)Phe), 2-chloro-phenylalanine (Phe(2Cl)), α-methyl-phenylalanine ((CαMe)Phe), 3,4-dimethoxy-phenylalanine (Phe(3,4-di OMe)), 4-carboxyphenylalanine (Phe(4COOH)), 4-nitrophenylalanine (Phe(4-$NO_2$)), 4-trifluoromethyl-phenylalanine (Phe(4-$CF_3$)), 4-tert-butyl-phenylalanine (Phe(4-tBu)), 3,4-dichloro-phenylalanine (Phe(3,4-diCl)), phenylglycine (Phg), (2S,5R)-5-phenyl pyrrolidine-2-carboxylic acid (Ppca), propargylglycine (Pra), homoproline (HoPro), β-homoproline (βHoPro), 2-quinoylalanine (2Qal), Na-methylglycine (Sar), homoserine (HoSer), 3-styryl-alanine (Sta), taurine (Tau), 4-thiazoylalanine (Tha), 3-(2-thienyl)alanine (2Thi), 3-(3-thienyl)alanine (3Thi), thiazolidine-4-carboxylic acid (Thz), thiazolidine-2-carboxylic acid (Thz(2-COOH)), tetrahydro-isoquinoline-3-carboxylic acid (3Tic), (R)-1,2,3,4-tetrahydroisoquinoline-3-carboxylic acid (Tic), 3,5-dinitrotyrosine (Tyr(3,5di $NO_2$)), 3-nitrotyrosine (Tyr(3-$NO_2$)), 3,5-diiodotyrosine (Tyr(diI)), and Nα-methyl-valine ((NMe)-Val), a phenylalanine analog, derivatives of lysine, and stereoisomers thereof (see, Liu and Lam, *Anal. Biochem.*, 295:9-16 (2001)). As such, the unnatural α-amino acids are present either as unnatural L-α-amino acids, unnatural D-α-amino acids, or combinations thereof.

The amino acids of the present invention can be in the D or L configuration. The amino acids of the cyclic peptide can all be in D or L configuration, or a combination thereof. In some embodiments, the amino acid configuration alternates between D and L. For example, when the cyclic peptide has 8 amino acid alternating between Lysine and Alanine, the Lysines can have the L configuration and the Alanines the D configuration, or vice versa. In some embodiments, the cyclic peptide includes alternating D and L amino acids.

The cyclic peptide can have any suitable number of amino acids. For example, the cyclic peptide can have from 6 to 20 amino acids, including 6, 7, 8, 9, 10, 11, 12, 13, 14, 15, 16, 17, 18, 19 or 20 amino acids. In some instances, the cyclic peptide can have more amino acids. In some embodiments, the cyclic peptide can have from 8 to 10 amino acids. In other embodiments, the cyclic peptide can have 8 amino acids. In some other embodiments, the cyclic peptide can have 10 amino acids.

In other embodiments, the cyclic peptide can have the formula:

wherein $X^1$ is a D-amino acid, $X^2$ is an L-amino acid, and x is an integer from 3 to 10.

In some embodiments, the cyclic peptide comprises alanine and lysine. In other embodiments, the cyclic peptide has the formula:

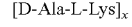

wherein x is an integer from 3 to 10. In some other embodiments, the cyclic peptide is [D-Ala-L-Lys]$_4$ or [D-Ala-L-Lys]$_5$. In still other embodiments, the cyclic peptide is [D-Ala-L-Lys]$_4$.

The cyclic peptides can be linked to a conjugate polymer to form a cyclic peptide conjugate. The conjugate polymer can be a hydrophilic polymer or a hydrophobic polymer. The conjugate polymer can be any suitable polymer, including, but not limited to, polyethyleneoxide (PEO), polystyrene (PS) and polymethylmethacrylate (PMMA).

In some embodiments, the conjugate polymer is a hydrophilic polymer. In other embodiments, the conjugate polymer is polyethyleneoxide (PEO), polystyrene (PS) or polymethylmethacrylate (PMMA). In still other embodiments, the conjugate polymer is polyethylene oxide (PEO).

The conjugate polymer and cyclic peptide are present in any suitable ratio. For example, the conjugate polymer can be present in excess to the cyclic peptide. Alternatively, the cyclic peptide can be present in excess to the conjugate polymer. The ratio of the conjugate polymer to the cyclic peptide can be 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1 or 5:1 (mol/mol). In some embodiments, the cyclic peptide conjugate includes the conjugate polymer and the cyclic peptide in a ratio of about 1:1 to about 4:1 (mol/mol).

The porous thin films are also prepared using a block copolymer where one block binds to the conjugate polymer and the second block does not substantially bind to the to conjugate polymer. In some embodiments, the block copolymer includes polymethylmethacrylate (PMMA) as the first block and polystyrene (PS) as the second block. The block copolymer can be any suitable molecular weight, including from about 1 kD to about 100 kD, preferably about 2, 3, 4, 5, 6, 7, 8, 9, 10, 15, 20, 25, 30, 35, 40, 45, 50, 60, 70, 80 or 90 kD. The first and second block can each have about the same molecular weight or different molecular weights.

The cyclic peptide conjugate and the block copolymer are mixed together in a suitable solvent. Any organic solvent is suitable for mixing, including, but not limited to, toluene, methylene chloride, and benzene. The cyclic peptide conjugate and block copolymer can be mixed at any suitable concentration and any suitable ratio. The mixture of the cyclic peptide conjugate and the block copolymer can be coated on any suitable substrate via methods known to one of skill in the art, such as spin-coating.

After mixing the cyclic peptide conjugate and the block copolymer, the cyclic peptides conjugates self-assemble to form a cyclic peptide nanotube. The self-assembly of the cyclic peptide nanotube can be promoted by heating, or occur in the absence of heating. In some embodiments, the mixture coated on the substrate annealed. The appropriate annealing temperature depends on the selection of the conjugate polymer and the block copolymer. The cyclic peptide nanotube that is formed can be any suitable length.

In other embodiments, the cyclic peptide nanotube can be formed by self-assembly of the cyclic peptide prior to conjugation with the conjugate polymer. In some other embodiments, the method also includes contacting the cyclic peptide and the conjugate polymer to form the cyclic peptide conjugate.

The present invention also provides a porous thin film composition prepared by the method of the present invention.

In other embodiments, porous thin film compositions of the present invention include a cyclic peptide nanotube having a plurality of cyclic peptide polymer conjugates each including a cyclic peptide and a conjugate polymer covalently linked to the cyclic peptide, wherein the cyclic peptide nanotube extends from a bottom surface of the porous thin film to a top surface of the porous thin film, and wherein the cyclic peptide nanotube has a pore diameter of about 0.5 to about 3 nm. The porous thin film composition also includes a block copolymer having a first block able to bind to the conjugate polymer and a second block that does not substantially bind to the conjugate polymer, wherein the porous thin film has a thickness of from about 10 nm to about 1000 nm. The porous thin film compositions of the present invention can also include a hexagonal distribution of the pores in the porous thin film.

IV. EXAMPLES

Materials. Fmoc-D-Ala-OH, Fmoc-L-Lys(Boc)-OH, polystyrene-(2-chlorotrityl) resin (loading: 1.5 mmol/g), and 2-(1H-benzotriazole-1-yl)-1,1,3,3-tetramethyluronium hexafluorophosphate (HBTU) were purchased from Nova Biochem. 2-Propanephosphonic acid anhydride (T3P) in DMF was purchased from Advanced ChemTech. Polystyrene-block-poly(methyl methacrylate) (PS-b-PMMA) and carboxylic acid-terminated polystyrene (PS-COOH) ($M_w$=3K, PDI 1.4) were purchased from Polymer Source. Two PS-b-PMMA BCPs with molecular weight of 37K-37K (called "LSM", PDI 1.07) and 57K-25K (called "CSM", PDI 1.07), respectively, were used. Carboxylic acid-terminated poly(ethylene oxide) (PEO) ($M_w$=3.3K, PDI 1.2) was purchased from RAPP POLYMERE. All reagents were purchased with the highest purity and used as received unless otherwise noted. The random copolymers of styrene and methyl methacrylate with 2% reactive benzocyclobutene (BCB) [P(S-r-BCB-r-MMA)]($M_w$=20.3K or 14.7K, PDI 1.2) were provided by T. P. Russell at the University of Massachusetts, Amherst.

Example 1

Synthesis of Cyclic Peptide Conjugate

The linear precursor to the cyclic octapeptide [D-Ala-L-Lys]$_4$ (8CP) was prepared with standard Fmoc-based (Fmoc=9-fluorenylmethoxycarbonyl) protocols for solid-phase peptide synthesis using a 2-chlorotrityl chloride resin preloaded with Fmoc-L-Lys(Boc)-OH. After cleavage of the linear octapeptide using 1% TFA in dichloromethane containing 5% triisopropyl silane, 8CP was cyclized head-to-tail using T3P and DIPEA. Boc-protecting groups were subsequently removed with a cleavage cocktail containing 95% TFA, 2.5% triisopropylsilane and 2.5% MilliQ water.

Carboxylic acid-terminated PEO was conjugated to 8CP by coupling to the s-amino groups of lysine residues with a polymer to 8CP feed ratio of 8. PEO-8CP was purified by extensive dialysis (regenerated cellulose, MWCO 6-8 kDa) against MilliQ water. PS-8CP was prepared using a similar protocol. For PMMA-8CP, the amine group of the lysine residues was first modified with the STP-ester of 4-azidovaleric acid. Alkyne terminated PMMA was coupled to 8CP using standard copper-mediated "click" chemistry. The excess of PMMA was removed by subjecting the reaction mixture to standard reaction conditions in the presence of an azido-modified Merrifield resin.

Figure 6:
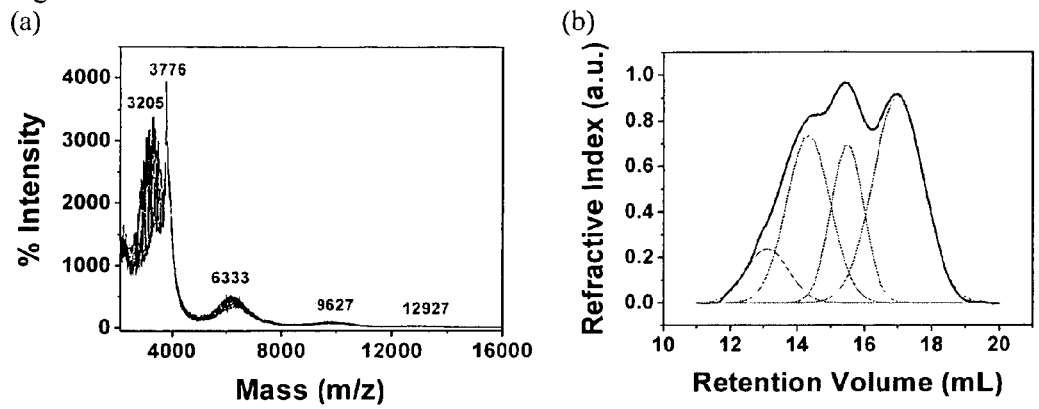
FIG. 6 shows (a) the MALDI-TOF mass spectrum of PEO-8CP used in present study, and (b) the size exclusion chromatogram of the dialyzed PEO-8CP using DMF containing 0.2% LiBr as eluent.
Figure 7:
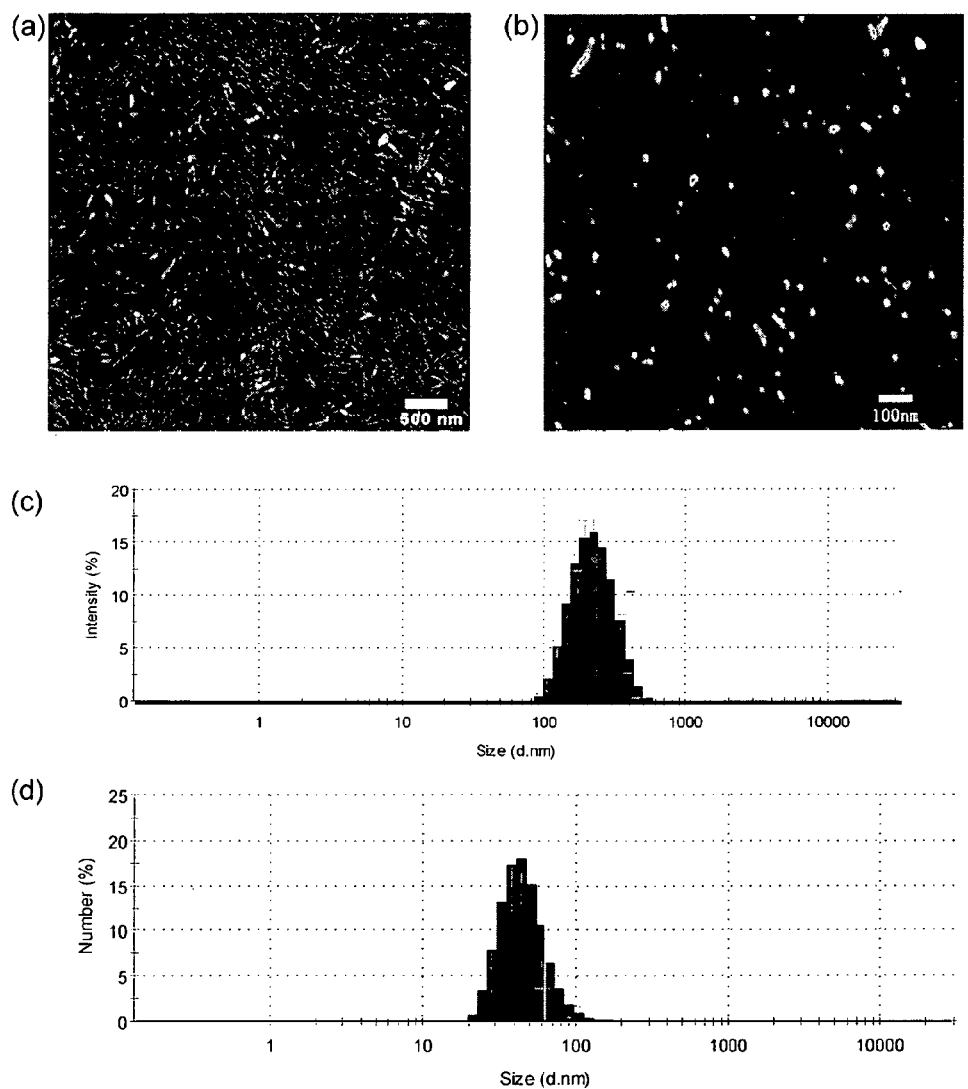
FIG. 7 shows (a) the SFM image of 8CPNs, (b) the SFM image of PEO-8CPNs, (c) the particle size distribution of 0.5 mg/mL PEO-8CP in toluene obtained by Dynamic Light Scattering (DLS), and (d) the particle size distribution of 0.5 mg/mL PMMA-8CP in toluene.
Figure 8:
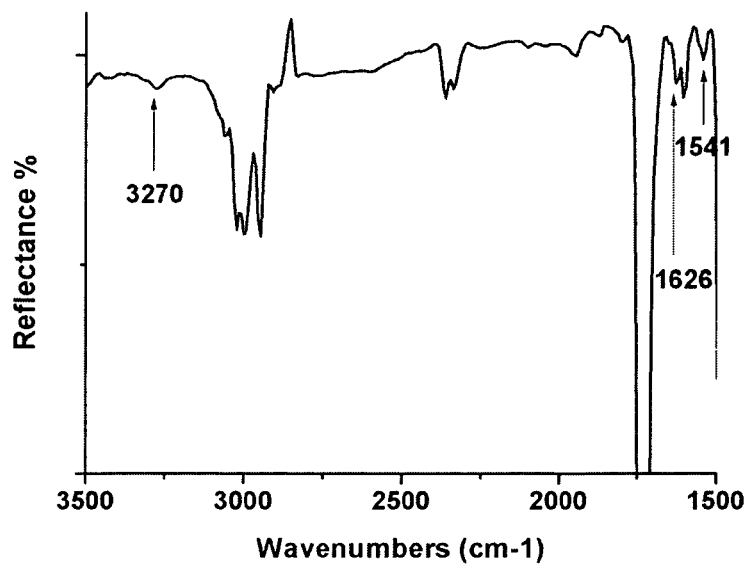
FIG. 8(a) shows the attenuated total reflectance (ATR)—FTIR spectrum of a thin film of a 8-CP-PS/LSM (3:10 wt ratio) blend and (b) is an AFM phase image of ~32 nm thin films of 8CP-PMMA/LSM (3:10 wt ration), where PMMA-covered CPNs phase separate from LSM.
Figure 8:
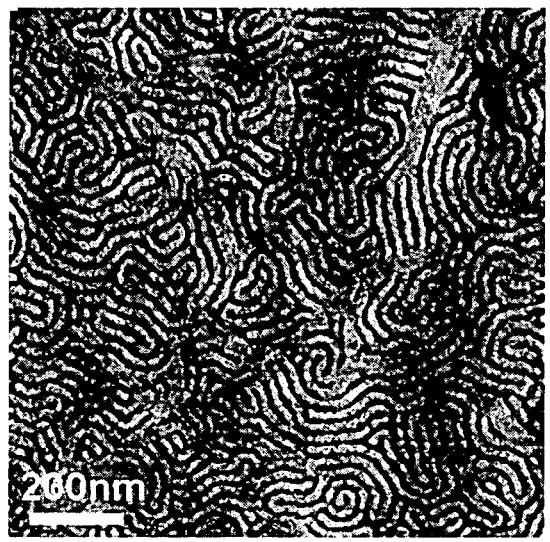

As shown in FIG. 1a, cyclic peptide (CP) is composed of an alternating sequence of D- and L-amino acids that stack to form nanotubes by an inter-ring hydrogen bonding. A CP with a sequence of ([D-Ala-L-Lys]$_4$) (called 8CP) was used. 8CPs stack to form ~0.7 nm diameter nanotubes (called 8CPNs). Carboxylic acid-terminated poly(ethylene oxide) (PEO) with a weight average molecular weight ($M_w$) of 3.3 KDa and a polydispersity (PDI) of 1.2 was attached to the 8CPs by reaction with the lysine residues. The resulting PEO-8CP conjugates have an average PEO:8CP ratio of 1.6 (FIG. 6). In toluene, PEO-8CPs form PEO covered cyclic peptide nanotubes (CPNs) (called PEO-8CPNs) that are ~200 nm in length and ~2.5-3 nm in diameter (FIG. 7). 8CPs conjugated with polystyrene (PS) ($M_w$=3 KDa, PDI=1.2) was prepared using similar protocols. Poly(methyl methacrylate) (PMMA) ($M_w$=5 KDa, PDI=1.1, avg. 3 PMMA chains per CP) were also prepared (FIG. 7c). See also Table 1.

TABLE 1

| Diam. (nm) | FWHM (nm) | |
|---|---|---|
| | % Intensity | |
| 227 | 100 | 68.7 |
| | % Volume | |
| 249 | 100 | 81.2 |
| | % Number | |
| 227 | 100 | 100 |

Example 2

Preparation of Porous Thin Film

Si substrates were modified using a random copolymer of styrene and methyl methacrylate as described previously (Science, 308, 236 (2005)). A ~8-10 nm thin film of [P(S-r-BCB-r-MMA)] was spin coated onto the substrate and subsequently annealed at 250° C. for 15 minutes to crosslink random brush. The brush layer was rinsed with toluene 3 times at 3000 rpm to remove uncrosslinked polymers.

Polymer-8CP conjugates and PS-b-PMMA BCPs were dissolved in toluene and mixed overnight. Thin films were prepared by spin casting a 1 wt % solution in toluene at 3000 rpm. The films were annealed at 178° C. under vacuum for 4 h and slowly cooled down to room temperature over 15 minutes. For TEM measurements, thin films were floated off the Si substrate by immersing in a 5 wt % HF solution, rinsed in DI water bath, and transferred onto a copper grid. Membranes for proton and gas transport measurements were prepared similarly onto commercially available membrane (HT Tuffryn, Pall Life Sciences) with an average diameter of 0.2 µm and thickness of 152 µm.

To macroscopically align CPNs, CP-polymer conjugates can be blended with PS-block-PMMA block copolymers (BCPs). One has a $M_w$ of 82 KDa (PDI=1.07), a PMMA volume fraction of ~0.5 and Ruins lamellar morphology (LSM). The other has a $M_w$ of 74 KDa (PDI=1.07), a PMMA volume fraction of ~0.3 and forms cylindrical morphology (CSM). LSM and CSM can be solution processed into thin films over various substrates having BCP microdomains oriented normal to the surface by either surface modification or applying an electric field.

Figure 2:
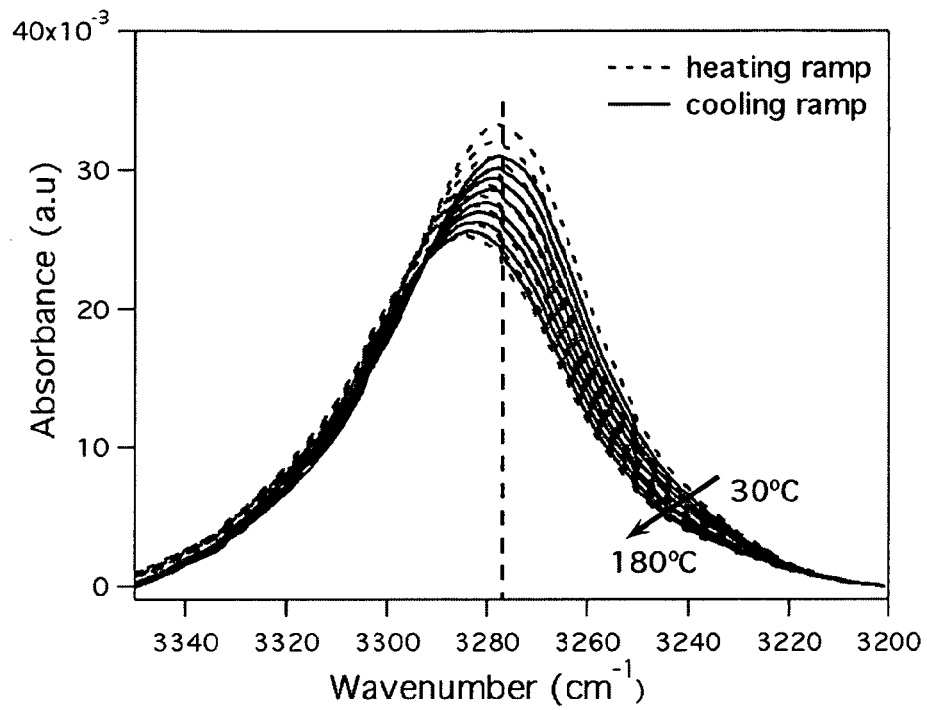
FIG. 2 shows results from in-situ FTIR studies on the growth of 8CPNs under thermal treatments.
Figure 2:
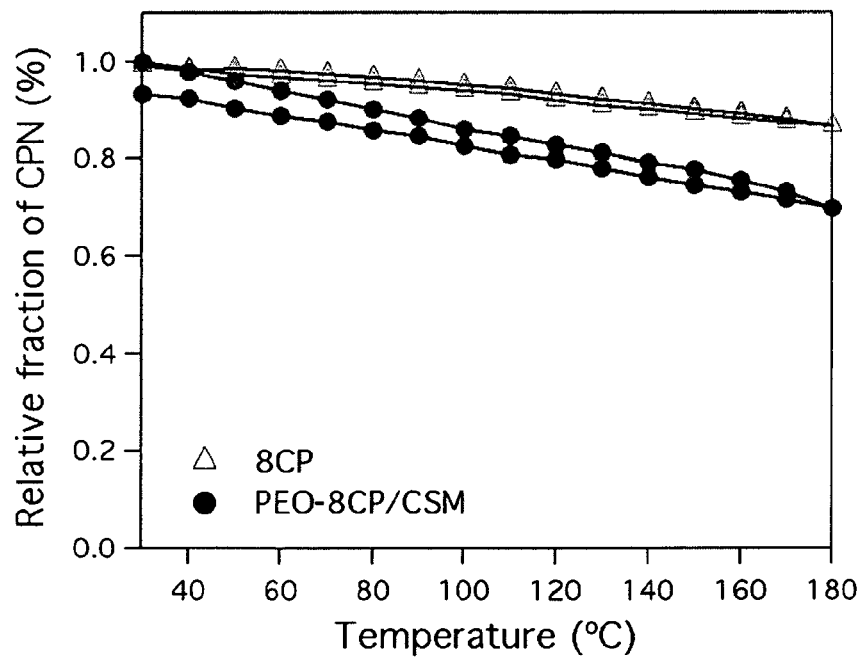
Figure 9:
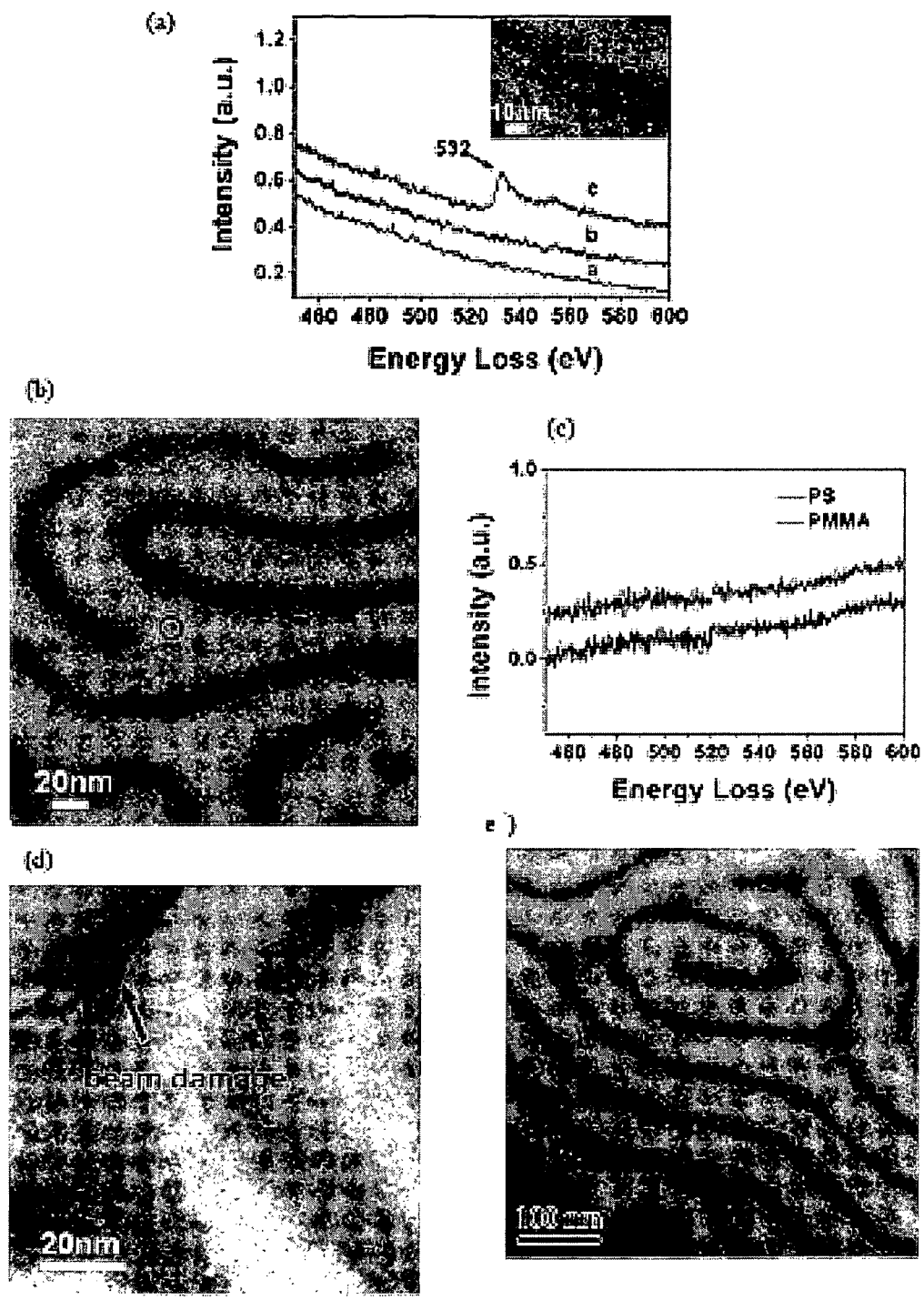
FIG. 9 shows (a) the HAADF-STEM image of a ~32 nm thin film of PEO-8CP/LSM at three regions indicated by black, blue and red circles, respectively that identify PEO, PS and PMMA, (b) the HAADF-STEM image of a ~32 nm thin film of LSM acquired with the probe size of 0.7 nm, (c) the EELS spectra collected from PMMA and PS lamellae indicated by blue and red circles, respectively, (d) the HAADF-STEM image of LSM thin film; and (e) the HAADF-STEM image of a ~32 nm thin film of PEO/LSM acquired with the probe size of 0.7 nm.

FIG. 2a shows a scanning force microscopy (SFM) image of a ~32 nm thin film of a PS-8CP:LSM (3:10 wt ratio) blend after thermal annealing. The Si substrates were modified with a ~10 nm film of a crosslinked random copolymer of styrene and methyl methacrylate to balance the interfacial interactions and orient BCP microdomains normal to the surface. PS-covered CPNs, a few hundred nanometers in length, are seen that phase separate from the LSM and orient parallel to the surface of the film. Without being held to one theory, increasing the molecular weight and the number of conjugated polymers for each CP suppresses CPN growth, reducing the average length of polymer-covered CPNs. PEO has weaker favorable interactions with PMMA and stronger non-favorable interactions with PS than PMMA. Without being bound to one particular theory, this provides a driving force to solublize PEO-8CP conjugates in the PMMA microdomains. FIG. 2c shows a high angle annular dark field scanning TEM (HAADF-STEM) image of a ~32 nm thin film of PEO-8CP:LSM (3:10 wt ratio). The electron energy loss spectra (EELS) (FIG. 2d and FIG. 9)) identify the different chemical constituents. PEO-8CPNs are selectively sequestered to the center of the PMMA lamellae. The magnified image in the inset of FIG. 2d shows a side view of a PEO-8CPN where the dark line in the center of the PEO-covered CPN indicates a hollow channel. This is consistent with previous observations of CPN. Similar results were observed in the blend of PMMA-CPs and PS-b-PEO. Without being bound to one particular theory, polymers conjugated to the CPNs effectively mediate the interaction between CPNs and their local environment, thereby selectively incorporating the polymer-covered CPNs within the BCP microdomain.

Figure 3:
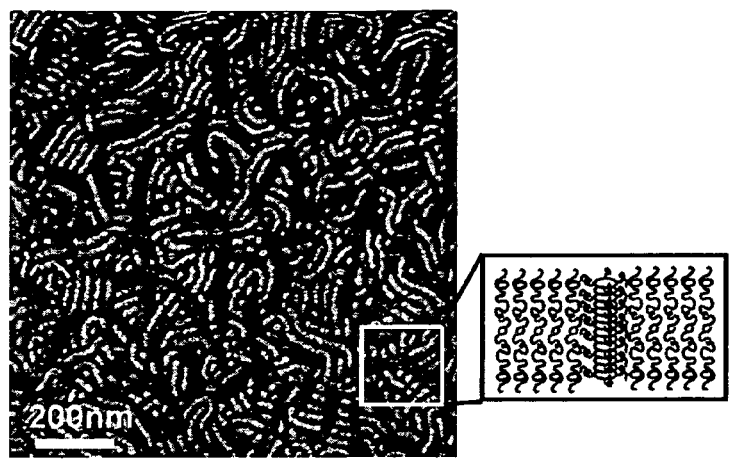
FIG. 3 shows AFM and STEM images of blends of polymer-8CP and BCP, showing that the interactions between the conjugated polymers and each BCP block are key parameters to direct their co-assembly.
Figure 3:
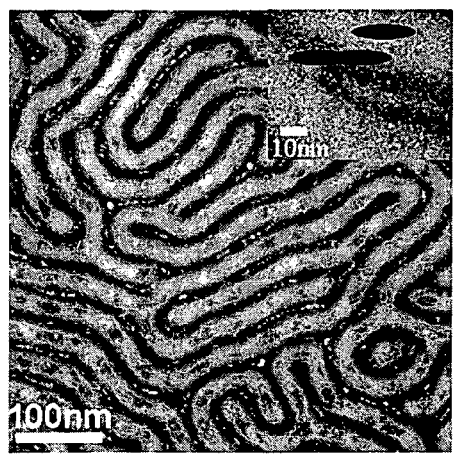
Figure 3:
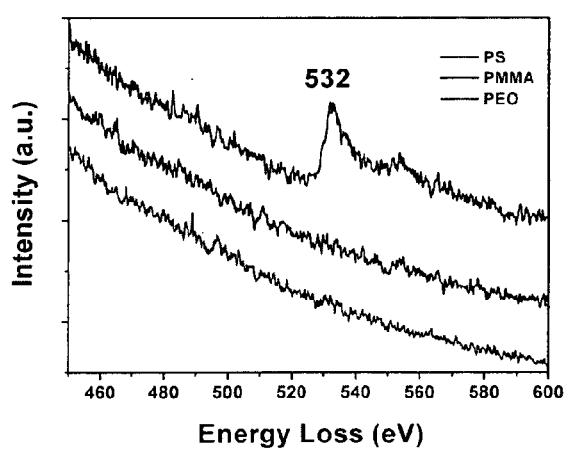
Figure 10:
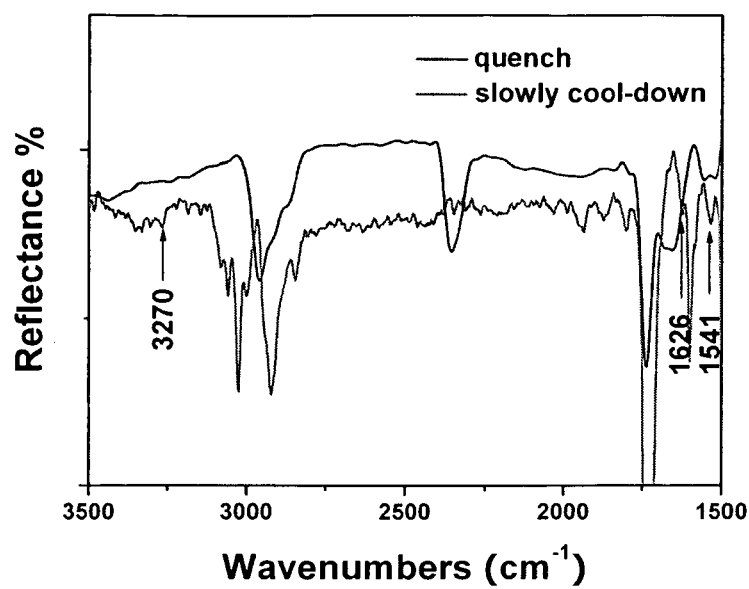
FIG. 10 shows the FTIR spectra of thin films a PEO-8CP/CSM blend (2:10 wt ratio) that have been quenched and slowly cooled-down from 178° C. to room temperature, respectively.
Figure 11:
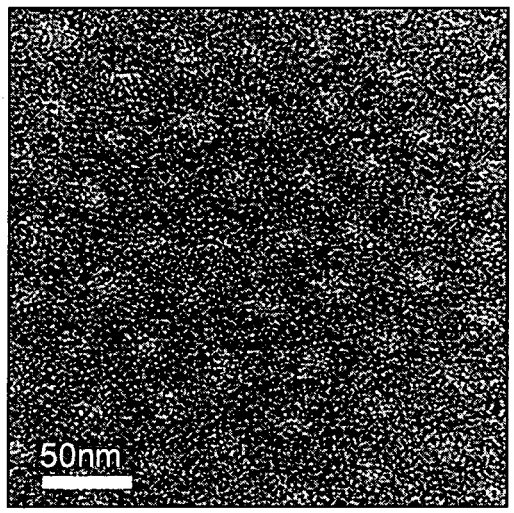
FIG. 11 shows TEM bright field image of a ~32 nm thin film of (a) CSM and (b) PEO/CSM blend taken under the same condition FIG. 4(b).
Figure 11:
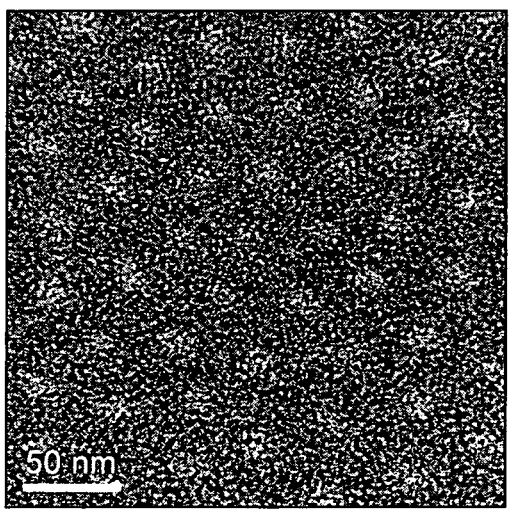

PEO-CPNs are randomly oriented within the PMMA lamellar microdomains, since there are no lateral geometric constrains to orient CPNs. FIG. 3a shows a SFM image of a ~32 nm thin film of PEO-8CP:CSM (2:10 wt ratio). Hexagonally packed core-shell cylinders oriented normal to the surface are seen, indicating the sequestration of PEO-8CPNs to the center of cylindrical PMMA microdomains. This was verified by a selective solvent washing using methanol. FIG. 3b shows the grazing incidence small angle x-ray scattering (GISAXS) pattern of the same film that provides strong evidence that the cylindrical microdomains of PMMA/PEO-8CPN orient normal to the film surface. In FIG. 3c, $q_y$ scans at $q_z$=0.023 Å$^{-1}$ show that the in-plane periodicity of the cylindrical microdomains increased from 37 to 41 nm with the addition of PEO-8CPs with CSM. Both SFM and GISAXS studies indicated a uniform incorporation of PEO-8CPNs within PMMA cylinders and the absence of PEO-8CPNs parallel to the surface. In toluene, PEO-8CPs form nanotubes of ~200 nm in length, much longer than the film thickness. The FT-IR spectra (FIG. 10) of two films of PEO-8CP/CSM that were quenched and slowly cooled from 178° C. show that PEO-8CPs are first incorporated within the PMMA cylindrical microdomains and subsequently reassemble into PEO-8CPNs upon cooling.

Figure 12:
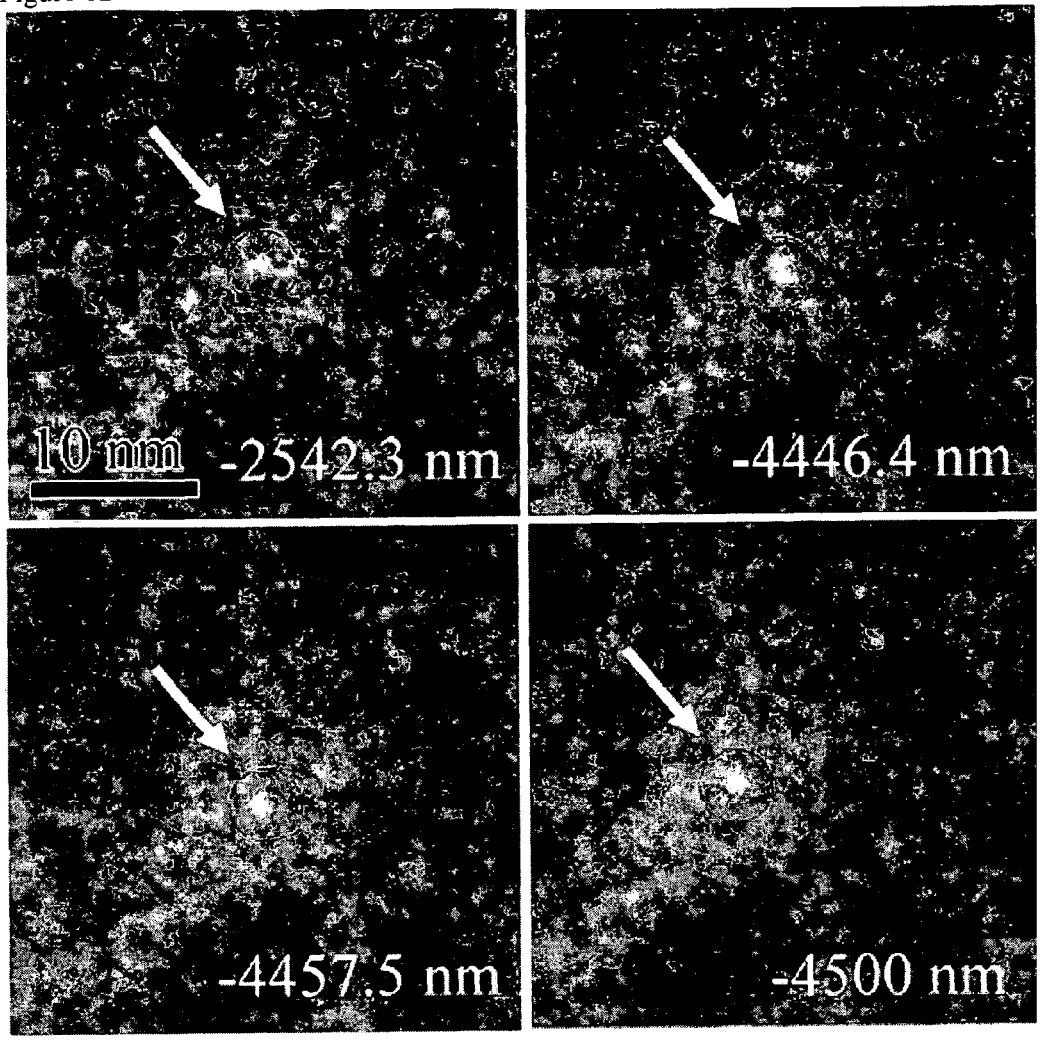
FIG. 12 shows a series of energy filtered under-focus bright filed TEM image of a ~32 nm thin film of PEO-8CP/CSM blend. The under-focus distance at which the image was collected is noted in each image. The white dot indicated by an arrow corresponds to the top-view of 8CPN. When the phase contrast was varied, the CPNs can still be seen, however, speckles disappear.
Figure 13:
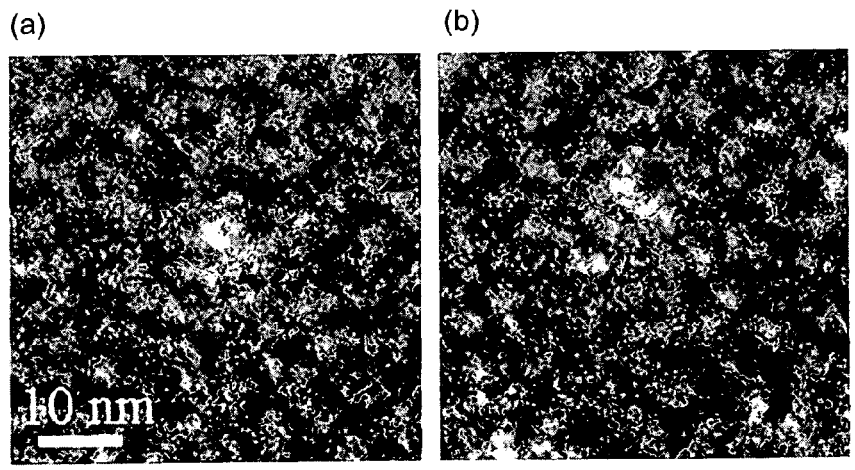
FIG. 13 shows the TEM images of a ~32 nm thin film of PEO-8CP/CSM blend before (a) and after (b) tilting two degrees along x- and y-axes. Due to the high aspect ratio of CPN (>40), a slight tilt prevents direct top-view of the CPNs and only CPNs oriented perpendicular to the surface of the film can be seen.
Figure 14:
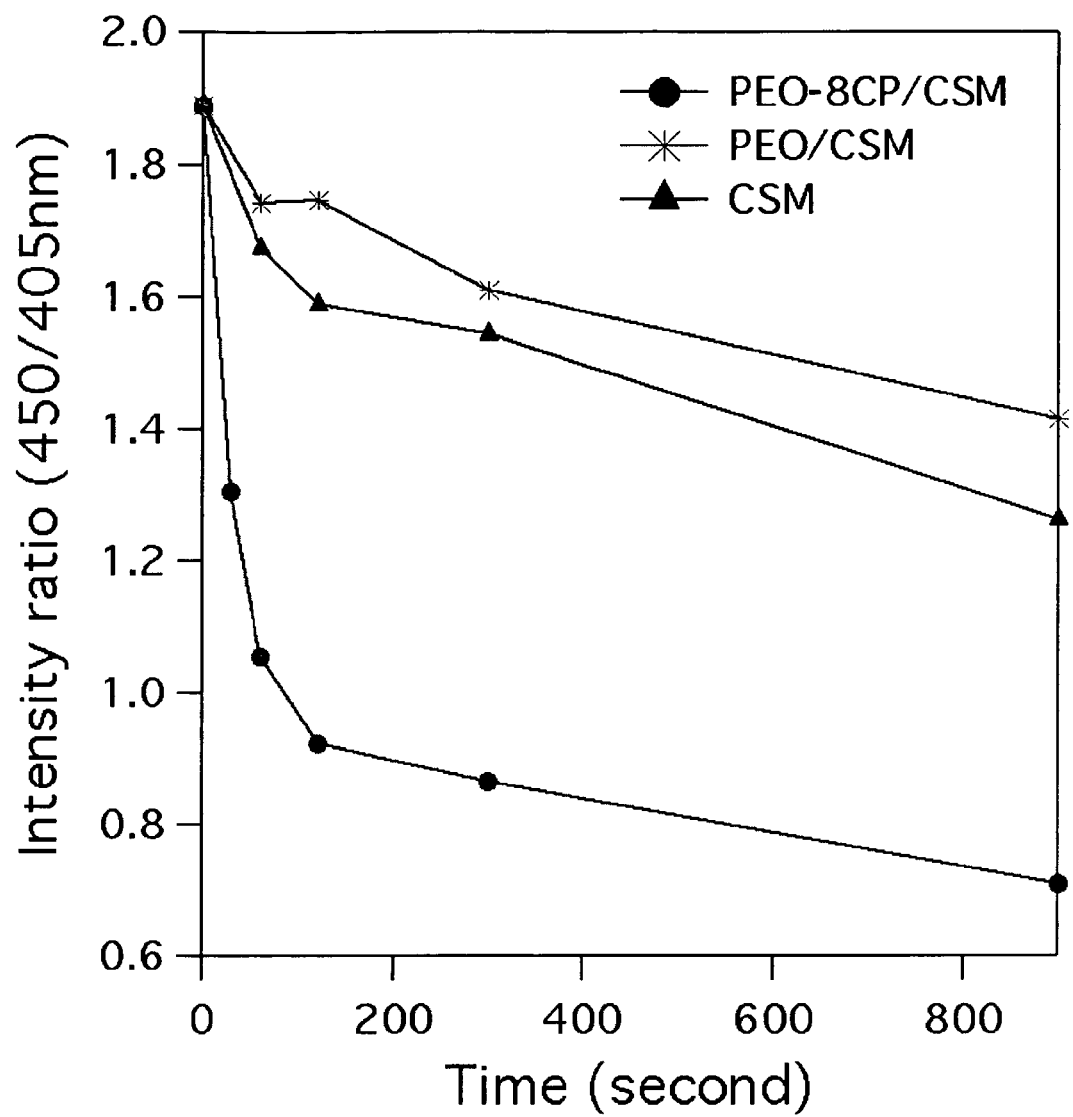
FIG. 14 shows the peak intensity ratio between 450 nm and 405 nm, an indication of pH value of the buffer solution, at different time for PEO-8CPN/CSM, PEO/CSM and CSM membranes, confirming proton transport through the 8CPNs.
Figure 15:
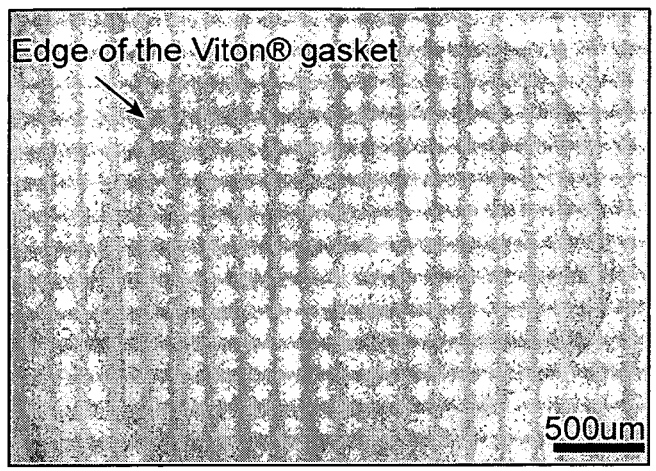
FIG. 15 shows optical images of a representative membrane tested at different magnifications.
Figure 15:
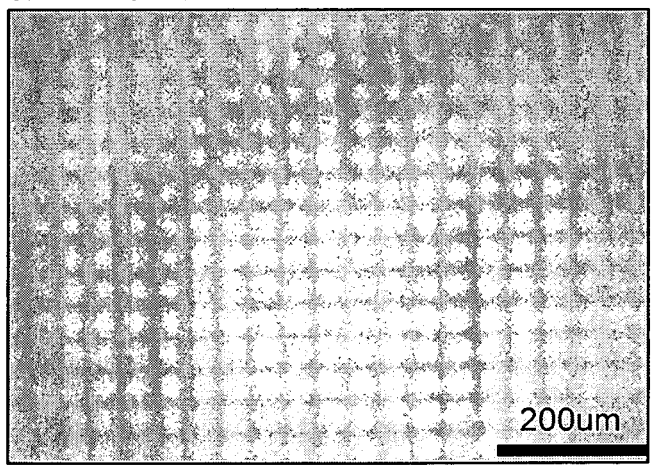

FIG. 3d shows the in-plane TEM image of a similar film of PEO-8CP/CSM blend. The image was taken under-focus to enhance contrast (FIG. 12). Hexagonally packed PMMA cylindrical microdomains oriented normal to the surface are seen. Sub-nanometer pores, arising from the PEO-8CPNs, are seen in the center of PMMA cylindrical microdomains, as shown in the inset. TEM images of a PEO:CSM blend (2:10 wt ratio) taken under identical conditions showed that PEO is localized to the center of PMMA microdomains (FIG. 12). Since the aspect ratio of the CPN is over 40, PEO-8CPNs must be straight, oriented normal to the film surface, and span across the entire film for the sub-nanometer pores to be observable (FIG. 13 and FIG. 14).

Figure 4:
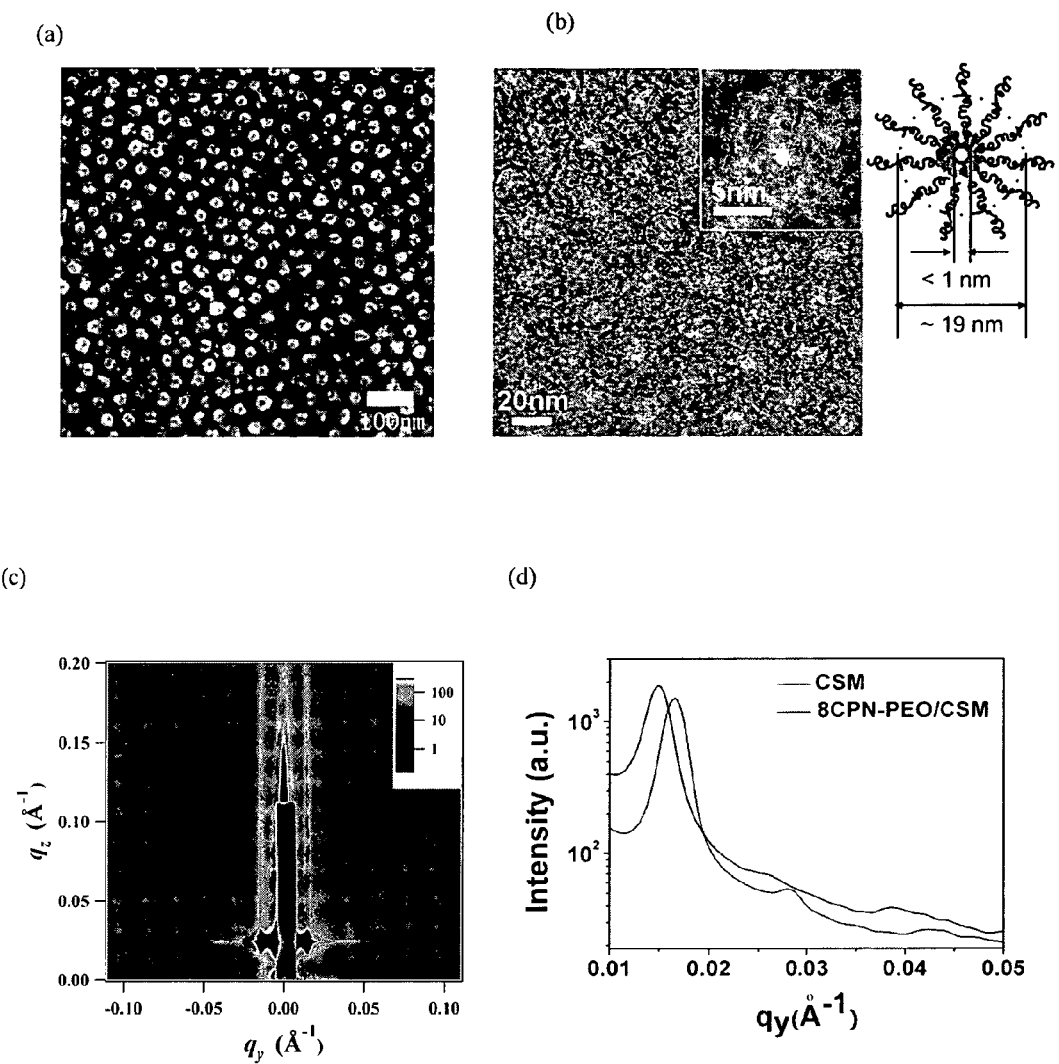
FIG. 4 shows the structural characterization of the thin films of blends of PEO-8CP and CSM, confirming hexagonally packed 8CPNs are oriented normal to the surface throughout the entire film thickness.
Figure 5:
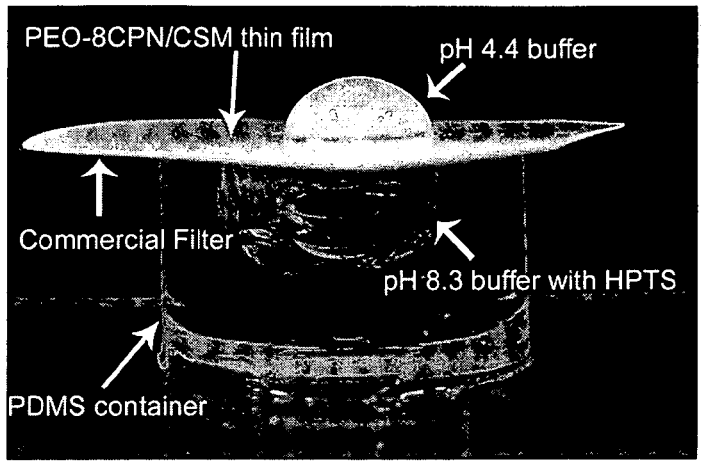
FIG. 5 shows proton transport measurement to confirm the CPNs are macroscopically aligned normal to the film thickness and span the film.
Figure 5:
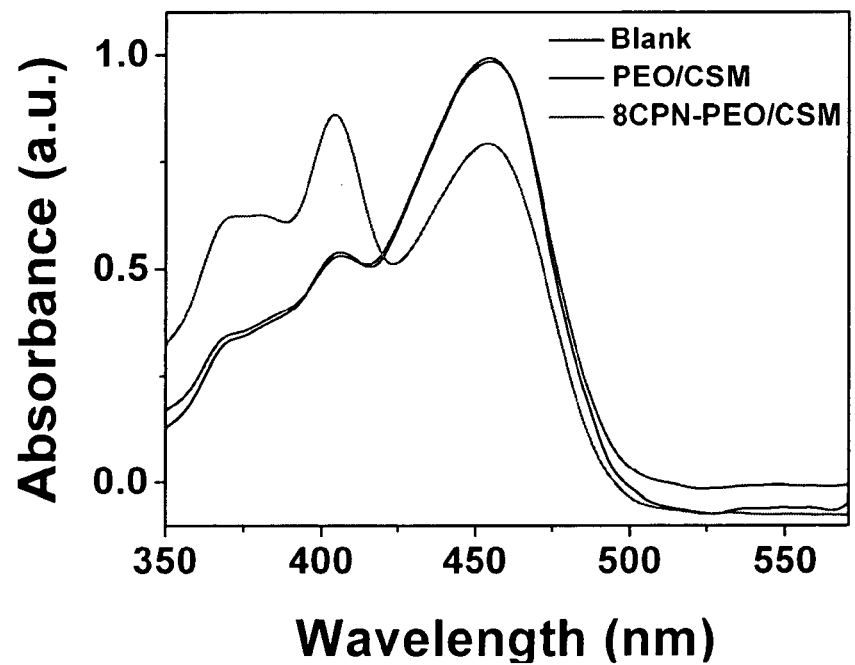
Figure 17:
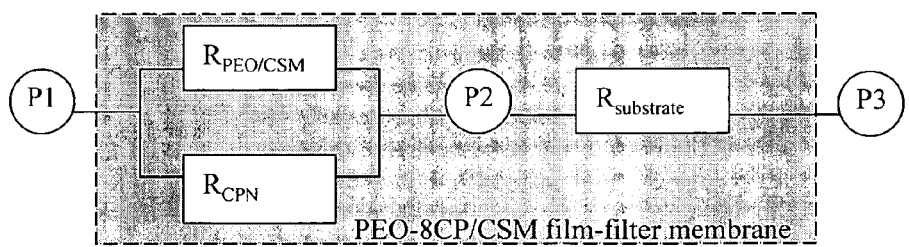
FIG. 17 shows that gas flow through the PEO-8CP/CSM membrane can be evaluated analogous to the current of an equivalent circuit.
Figure 18:
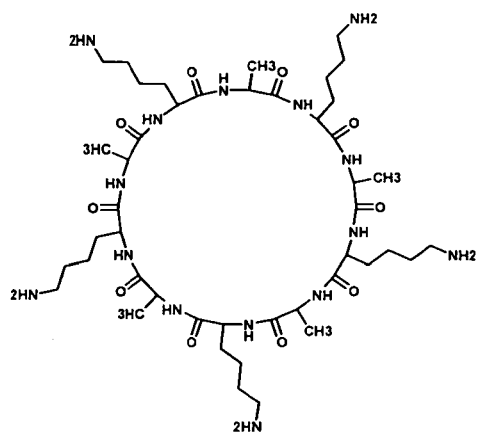
FIG. 18 shows (a) the chemical structure of 10CP, (b) the diameter of the interior is approximately 1.1 nm, and (c) the AFM image of a film containing 10CP-PEO nanotubes oriented normal to the surface.
Figure 18:
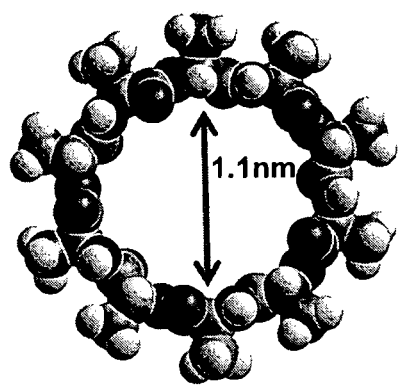
Figure 18:
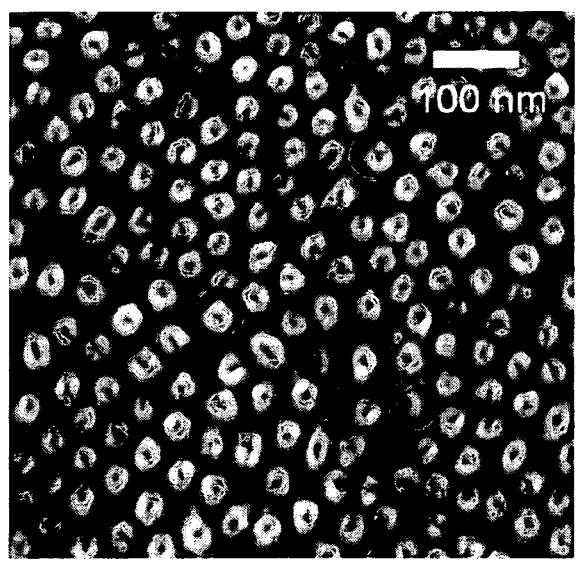

To further confirm the CPNs span across entire film thickness, proton transport measurements were performed by separating pH 4.4 buffer solutions from aqueous pH-sensitive dye, 8-hydroxypyrene-1,3,6-trisulfonic acid trisodium salt (HPTS) solutions (pH=8.3) with a thin film of PEO-8CPN/CSM processed on a commercial filter and, as a control, a thin film of PEO/CSM, as shown FIG. 4a. FIG. 4b shows the UV-vis spectra of the HPTS buffer solutions in both cases. The PEO/CSM film effectively blocks proton transport and no change in the UV-vis spectrum was observed. For PEO-8CPN/CSM, though, a pH change can be seen within a minute. Gas transport of the same membrane was tested after the proton transport measurement to ensure the membrane integrity (FIG. 17). Based on structural characterization in FIG. 3, it is evident that proton transport through the CPNs occurred. Although the diameter of 8CPN is well established previously, counter ion blocking experiments using tetrabutylammonium bromide were also performed to further verify size-selective transport of CPNs.

PEO-8CP conjugates co-assembled with PS-b-PMMA and lead to sub-nanometer channels that penetrate through the film with an areal density of $3 \times 10^{14}/m^2$. Such sub-nanometer porous films are structurally well defined and we carried out gas transport measurements to study mass transport through confined geometries. In comparison to the transport rate calculated using Knudson diffusion model, markedly enhanced gas molecule transport through sub-nanometer CPNs was observed for $CO_2$ and neopentane as shown in Table 2.

TABLE 2

Area percentage of PEO-8CPs with different number of PEO attached to each CP.

| Molecular weight | Area (%) | Number of arms |
|---|---|---|
| 3133 | 41.37 | 1 |
| 6263 | 20.57 | 2 |
| 9399 | 28.96 | 3 |
| 12969 | 9.10 | 4 |

Grazing incidence small angle x-ray scattering (GISAXS) measurements were performed at beamline 7.3.3 at the Advanced Light Source (ALS) at Lawrence Berkeley National Laboratory (LBNL) and at beamline 8-ID Advanced Photon Source (APS) at Argonne National Lab. An X-ray beam was directed at the sample at a grazing incident angle slightly above the critical angle of the polymer film. The scattered intensity was detected using a two-dimensional CCD camera with image sizes of 2304×2304 pixels.

AFM images were collected on the same samples used in the GISAXS experiments. Tapping mode SFM was used to study the thin film topography using a Molecular Imaging PicoSPM II with a PicoScan 2500 controller. Silicon cantilevers (RTESP from Veeco, Inc.) with a resonant frequency of 255 Hz were used.

FTIR and ATR-FTIR measurements were performed using a NICOLET 6700 FT-IR Spectrometer. For ATR-FTIR measurements, thin films with a thickness of ~100 nm were used to achieve good signal-to-noise ratio. For in-situ FTIR, the samples were cast between two NaCl pellets. The heating/cooling rate is 20 degree per minute and each spectrum was collected 5 minutes after teaching targeted temperature.

TEM experiments were carried out at an accelerating voltage of 200 KeV using a JEOL 2100F STEM/TEM equipped with a Gatan Erlangshen ES500W, an Orius SC1000 CCDs, a Gatan Tridiem energy filter system, and a Gatan 806 high angle angular dark field (HAADF) STEM detector. For the STEM analysis, a 0.7 nm of probe size, 40 μm of condenser aperture, and 7 cm of camera length of HAADF detector were used.

Proton transport measurements were carried out using a setup shown in FIG. 4a. Briefly, 150 μL of a 10 μM solution of HPTS (8-Hydroxypyrene-1,3,6-trisulfonic acid trisodium salt) in 25 mM potassium phosphate buffer at pH 8.3 was added to a molded, transparent PDMS vessel. After covering the vessel with a prepared membrane, 50 μL of 25 mM potassium phosphate buffer at pH 4.4 was introduced to the top of the membrane. Afterward, the UV-vis spectrum of the HPTS solution was recorded using a Hewlett-Packard 8453 spectrophotometer (FIG. 14).

Figure 16:
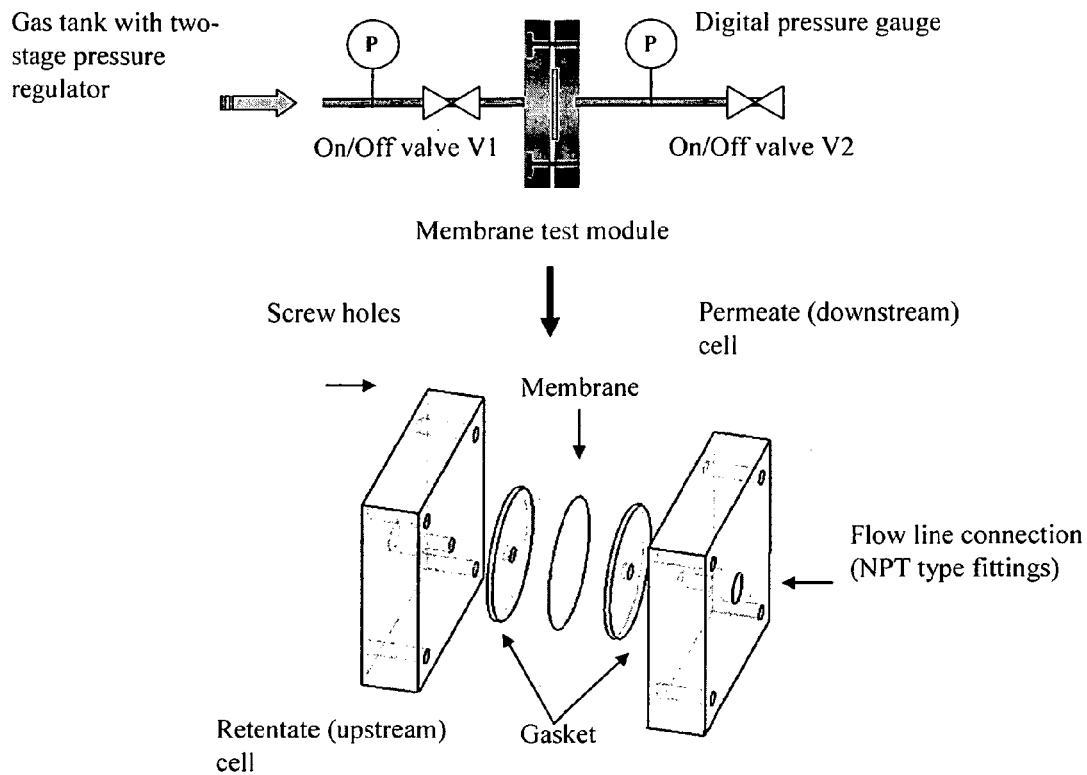
FIG. 16 shows the experimental setup for membrane permeability measurements.

Membrane Permeability. The membrane was sandwiched between two Viton® gaskets with a ⅛" hole at the center (see FIG. 16). The module was screw tighten. Measurements were carried out in the following procedure: First, valve V1 was closed and valve V2 was opened. After the upstream gas pressure was regulated to the specified pressure (in this case 1.5 psig), V1 was opened. V2 was then closed and the timer was started. The permeate cell pressure began to rise from 0 psig with time.

Permeance (Π) of a membrane is defined as:

$$J = \Pi(P_{retentate} - P_{permeate}) \quad \text{(Equation 1)}$$

where J is the molar flux (kmol/m$^2$) of the gas through the membrane, $P_{retentate}$ and $P_{permeance}$ are pressures of the retentate (upstream) cell and the permeance (downstream) cell, respectively.

Based on mass balance, the expression for permeance of the membrane can be derived (Ind. Eng. Chem. Res. 36, 2924 (1997)).

$$\Pi = \frac{V}{A \cdot R_u \cdot T \cdot t} \ln\left[\frac{P_{retentate}}{P_{retentate} - P_{permeance}(t)}\right] \quad \text{(Equation 2)}$$

where V is the volume of the permeate cell, A is the membrane area exposed to the gas stream, $R_u$ is the universal gas constant, T is the temperature, $P_{permeance}(t)$ is the pressure of permeance cell at an instance time (t) during the measurement. All parameters are in SI units. Pressures here are gauge pressures in the unit of Pascal. Utilizing equation (Equation 4) and the experimental data of $P_{permeance}(t)$, the permeance of each membrane (Π) were obtained and listed in Table 3. Measurements were also performed using a commercial filter (the substrate of the membrane) and the result was consistent with the factory specified value. Note that values listed in Table 3 are the "overall permeance" for each membrane including the polymer film and the substrate filter. The "overall permeance" of the membrane is different from the permeance of the sub-nanometer pores ($\Pi_{CPN}$) listed in Table 4.

TABLE 3

| membrane gas type | "overall permeance" (Π) [mol/m$^2$sPa] | Number of samples |
|---|---|---|
| PEO/CSM CO$_2$ | 3.46*10$^{-6}$ ± 6.54*10$^{-7}$ | 11 |
| PEO-8CPN/CSM CO$_2$ | 7.86*10$^{-6}$ ± 8.97*10$^{-7}$ | 11 |
| PEO-8CPN/CSM Neopentane | 6.00*10$^{-6}$ ± 4.21*10$^{-7}$ | 8 |

Gas permeance of sub-nanometer CPN pores is on the order of 10$^{-6}$ mol/m$^2$sPa, which is over four orders of magnitude greater than what predicted from the classical gas flow theory. This indicates that gas transport through sub-nanometer CPN is ballistic in nature, which can be described by the Knudsen diffusion theory.

From free molecule flow theory, the Knudsen diffusion gas molar flux through a single pore is (Mills, A. F. Mass Transfer, Prentice-Hall Inc. New Jersey, (2001)):

$$J_{pore,Knudsen} = \frac{2}{3}\left(\frac{8}{\pi M R_u T}\right)^{1/2}\left(\frac{r_p}{L_f}\right)(\Delta P), \quad \text{(Equation 3)}$$

where M is gas molecular weight, $R_u$ is the universal gas constant. T is the temperature (assumed 300 K), $r_p$ is pore radius, $L_f$ is length of the pore, and $\Delta P$ is the pressure difference across the pore.

From definition, the permeance of a single CPN pore based on Knudsen diffusion model is given by:

$$\Pi_{pore,Knudsen} = \frac{2}{3}\left(\frac{8}{\pi M R_u T}\right)^{1/2}\left(\frac{r_p}{L_f}\right) \quad \text{(Equation 4)}$$

The permeance of CPN pores per unit membrane area calculated by Knudsen diffusion model is thus:

$$\Pi_{CPN,Knudsen} = a_{pore}\Pi_{pore,Knudsen} \quad \text{(Equation 5)}$$

$$= \frac{2}{3}\left(\frac{8\pi}{M R_u T}\right)^{1/2}\left(\frac{N_p r_p^3}{L_f}\right),$$

where $a_{pores}$ = area fraction of CPN pores = $N_p(\pi r_p^2)$, and $N_p$ is the number of pores/unit membrane area.

Gas flow through the PEO-8CP/CSM membrane can be evaluated analogous to the current of an equivalent circuit as shown in FIG. 17, where $$J_{PEO\text{-}8CP/CSM} = \frac{(P_1 - P_3)}{(R_{CPN}^{-1} + R_{PEO/CSM}^{-1})^{-1} + R_{substrate}} \quad \text{(Equation 6)}$$

$$= \Pi_{PEO\text{-}8CP/CSM}(P_1 - P_3),$$

$$R_{PEO/CSM} = \frac{1}{(1 - a_{pores})\Pi_{PEO/CSM}}, \quad R_{CPN} = \frac{1}{\Pi_{CPN}},$$

and $R_{substrate} = \frac{1}{\Pi_{substrate}}$.

The permeance of CPN pores per unit membrane area from measurements ($\Pi_{CPN}$) can thus be obtained by using Equation (Equation 6) and experimental data (mean values) of $\Pi_{PEO/CSM}$, $\Pi_{PEO\text{-}8CP/CSM}$ and $\Pi_{substrate}$.

TABLE 4

Enhancement of gas flow rate through PEO-8CPN/CSM membranes in comparison to the theoretical values calculated using Knudsen diffusion model

| Gas type | $\Pi_{CPN, experiment}$ [mol/m²sPa] | $\Pi_{CPN, Knudsen}$ [mol/m²sPa] (Equation S14-3) | Enhancement over Knudsen diffusion |
|---|---|---|---|
| CO₂ | 5.69*10⁻⁶ | 1.17*10⁻⁷ | 48.63 |
| Neopentane | 3.26*10⁻⁶ | 9.11*10⁻⁸ | 35.78 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of making a porous thin film, the method comprising:
    contacting a substrate with a mixture comprising
        a plurality of cyclic peptide conjugates each comprising a cyclic peptide and a conjugate polymer covalently linked to the cyclic peptide, and
        a plurality of block copolymers each block copolymer comprising a first block able to bind to a conjugate polymer of the plurality of cyclic peptide conjugates and a second block that does not substantially bind to the conjugate polymer; and
    annealing the mixture, such that the plurality of cyclic peptide conjugates self-assemble vertically in horizontal planes to form a plurality of cyclic peptide nanotubes perpendicular to the substrate and extending from a top surface to a bottom surface of the porous thin film.

2. The method of claim 1, wherein the cyclic peptide comprises alternating D and L amino acids.

3. The method of claim 1, wherein the cyclic peptide comprises alanine and lysine.

4. The method of claim 3, wherein the cyclic peptide has the formula:

[D-Ala-L-Lys]$_x$ wherein x is an integer from 3 to 10.

5. The method of claim 4, wherein the cyclic peptide is selected from the group consisting of [D-Ala-L-Lys]₄ and [D-Ala-L-Lys]₅.

6. The method of claim 4, wherein the cyclic peptide is [D-Ala-L-Lys]₄.

7. The method of claim 1, wherein the conjugate polymer is a hydrophilic polymer.

8. The method of claim 1, wherein the conjugate polymer is selected from the group consisting of polyethylene oxide (PEO), polymethylmethacrylate (PMMA) and polystyrene (PS).

9. The method of claim 8, wherein the conjugate polymer is polyethylene oxide (PEO).

10. The method of claim 1, wherein the cyclic peptide conjugate comprises the conjugate polymer and the cyclic peptide in a ratio of about 1:1 to about 4:1.

11. The method of claim 1, further comprising coating the surface of the substrate with a coating polymer prior to contacting with the mixture, the coating polymer comprising at least one of a random copolymer of styrene (S), methylmethacrylate (MMA) and benzocyclobutene (BCB).

12. The method of claim 11, further comprising annealing the coating polymer.

13. A method of making a porous thin film, the method comprising:
    contacting a substrate with a mixture comprising a plurality of cyclic peptide conjugates each comprising a cyclic peptide and a conjugate polymer covalently linked to the cyclic peptide, and a plurality of block copolymers each block copolymer comprising a first block able to bind to a conjugate polymer of the plurality of cyclic peptide conjugates and a second block that does not substantially bind to the conjugate polymer; and
    annealing the mixture, such that the plurality of cyclic peptide conjugates self-assemble vertically in horizontal planes to form a plurality of cyclic peptide nanotubes perpendicular to the substrate and extending from a top surface to a bottom surface of the porous thin film, and wherein the plurality of block copolymers are arranged in the horizontal planes and extend substantially radially from the plurality of cyclic peptides.

14. A porous thin film comprising:
    a plurality of cyclic peptide conjugates each comprising a cyclic peptide and a conjugate polymer covalently linked to the cyclic peptide; and
    a plurality of block copolymers each block copolymer comprising a first block able to bind to a conjugate polymer of the plurality of cyclic peptide conjugates and a second block that does not substantially bind to the conjugate polymer, wherein the plurality of cyclic peptide conjugates self-assemble vertically in horizontal planes to form a plurality of cyclic peptide nanotubes perpendicular to the substrate and extending from a top surface to a bottom surface of the porous thin film.

15. The porous thin film of claim 14, wherein the plurality of block copolymers are arranged in the horizontal planes and extend substantially radially from the plurality of cyclic peptides.

* * * * *